United States Patent [19]
Bahrton

[11] 3,982,535
[45] Sept. 28, 1976

[54] SIGNAL DEVICE FOR DIALYSIS APPARATUS

[76] Inventor: Per Svante Bahrton, Lojovagen 19, S-181 47 Lidingo, Sweden

[22] Filed: Mar. 4, 1975

[21] Appl. No.: 555,192

[30] Foreign Application Priority Data
Mar. 15, 1974 Sweden .............................. 7403545

[52] U.S. Cl. ...................... 128/214 E; 128/DIG. 3; 210/90; 210/128
[51] Int. Cl.² ......................................... A61M 1/03
[58] Field of Search ........ 128/214 R, 214 C, 214 E, 128/214 F, 214.2, DIG. 3; 210/90, 121, 123, 128

[56] References Cited
UNITED STATES PATENTS

| | | | |
|---|---|---|---|
| 3,091,239 | 5/1963 | Moeller | 128/214 F |
| 3,478,184 | 11/1969 | Cofoid | 200/84 |
| 3,543,752 | 12/1970 | Hesse et al. | 128/214 E |
| 3,731,680 | 5/1973 | Wright et al. | 128/214 E |
| 3,756,234 | 9/1973 | Kopp | 128/214 E X |

Primary Examiner—Dalton L. Truluck
Attorney, Agent, or Firm—Flynn & Frishauf

[57] ABSTRACT

A dialysis apparatus for machines such as artificial kidneys and heart-lung machines has a warning device activated to prevent air bubbles from entering the blood circulation system of the patient and controlled by the vertical position of a float in a float chamber where air is separated from the blood. The warning signal is triggered when the air/blood volume ratio in the chamber is increased so that the float sinks and closes off the outlet at the bottom portion of the chamber. Continued blood supply to the chamber compresses the air therein and the corresponding pressure increase is detected and used to generate a warning signal.

7 Claims, 1 Drawing Figure

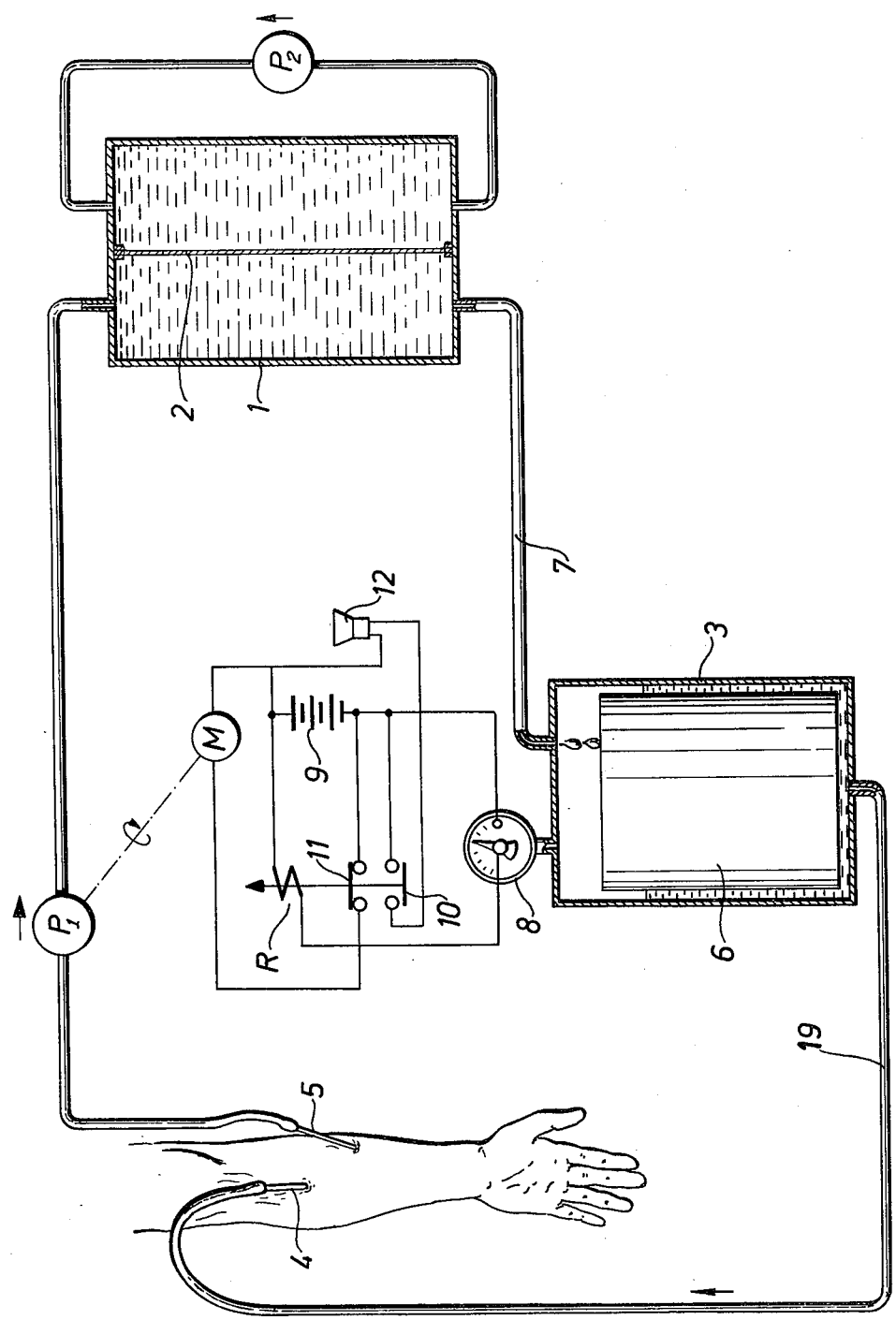

SIGNAL DEVICE FOR DIALYSIS APPARATUS

The present invention relates to a signal device for dialysis apparatus of the type generally referred to as an artificial kidney, a heart-lung machine and the like, comprising a pump which positively circulates blood through a circuit, part of which is constituted by a portion of the blood circulation system of the patient. The blood also passes through a float chamber in which air is separated from the blood and the float of which is arranged so that the blood supply to the patient is interrupted by the closing of an outlet valve when the amount of air in the float chamber exceeds a predetermined threshold value. When this occurs, signal means are activated and generate an alarm signal informing the staff operating the machine about the occurrence.

In prior art apparatus of the type above generally described the alarm signal is triggered optically. The wall of the float chamber in such a device consists of a transparent material, e.g. an artificial resin. Located at two diametrically opposite points outside the chamber wall are a light source and a photocell. In the normal state the float which is floating on the blood in the float chamber obstructs any passage of light from the light source to the photocell. However, should the blood volume in the chamber be reduced so that the float cannot remain floating it sinks to a position in which a light beam can freely pass above the top end of the float and reach the photocell whereby the latter generates an electrical pulse which in turn triggers any suitable warning device.

Apparatus of the prior art type above referred to suffer from several serious disadvantages the most prominent of which is the following one. The float chamber is connected in the patient blood circuit immediately upstream of the cannula through which the blood is reintroduced into the patient after having been relieved of secretion products. Blood is supplied to the float chamber from the artificial kidney or the corresponding machine and that supply takes place at the top portion of the float chamber so that the blood will drip down into the float chamber, air being separated in the process. However, it has been observed that above the level of the blood liquid there is frequently formed what is generally called blood foam and which consists of a mixture of blood and air. That foam is deposited on the walls of the float chamber vessel, thereby reducing their transparency to light. This results in difficulties as far as the adjustment of the sensitivity of the photocell is concerned and in serious cases foam may deposit in such heavy layers that the photocell becomes incapable of detecting a downward movement of the float caused by a large relative amount of air in the vessel. As is easily understood, this failure is the result of an insufficient illumination of the photocell due to the increased light emission resistance caused by the foam. It should be inserted here that it also belongs to the art to detect the presence of air bleeds by the aid of a photocell mounted close to a portion of the tube or hose through which the blood passes. While it is possible in that way to detect relatively large air bleeds, smaller ones escape detection. However, even very small air bleeds can later on by coalescence form bigger ones, the presence of which entail serious risks to the patient.

A general object of the invention is to provide a signal device the operation of which is independent of the safe function of light transmission through the walls of the float chamber.

A more specific object of the invention is to provide a signal device the safe operation of which does not require regular inspection, cleaning or adjustment of its various components.

A further object of the invention is to realize the objects above referred to by means of a device simultaneously capable of detecting the presence of a large volume of separated air formed by the cumulative effect of a multiplicity of small air bleeds, the individual presence of which cannot be detected.

SUMMARY OF THE INVENTION

The invention is based on the realization that all the objectives and advantages above referred to are attainable if the alarm signal is not triggered optically but by build-up of the pressure of the air in a float chamber containing a float that occurs upon the closure of an outlet valve, the outlet valve being closed by means of the float.

In a preferred embodiment of the invention the density of the float is matched so as to be slightly less than the density of the blood in the float chamber. The advantage resulting therefrom will be explained below.

In order for a device of the type here under discussion to yield maximum safety and efficiency two conditions have to be satisfied. Firstly, when in its bottom position the float must always interrupt the blood supply to the patient. Secondly, it is naturally equally vital that such a discontinuation of the blood supply triggers a warning signal. A third desideratum is that in such a situation the pump transporting blood from the patient to the artificial kidney or the like is always automatically stopped. Such an automatic stopping can easily be realized in a device according to the present invention which will be discussed below. It should, however, first be emphasized that the invention is based on the realization that it is feasible to trigger the warning signal in response to the increase of the pressure of the air collected in the top portion of the float chamber, which increase is the initial result of a discontinued blood transport. It should also be observed that this pressure increase occurs completely independently of whether blood foam is present or not, which means that the corresponding phenomenon can no longer cause any detection problems. This in turn means not only that the use of a photocell becomes superfluous but also that the float chamber walls may be made of any suitable material since there is no longer any requirement that the walls be transparent to light. The advantage accompanying matching the density of the float so that it is but insignificantly less than the mean value of the density of the blood liquid resides in that the major portion of the float will always remain submerged in the blood liquid. This in turn results in that when the outlet from the chamber is closed by the float in the way that its bottom end acts like a valve member and sealingly contacts a valve seat which can simply be in the form of the flat bottom of the float chamber, the blood level will be at a considerable height above the outlet or, stated in other words, the risk that air bleeds might enter the blood system of the patient has been avoided by a considerable safety margin.

BRIEF DESCRIPTION OF THE DRAWINGS

The single FIGURE illustrates a preferred embodiment of the invention.

DETAILED DESCRIPTION OF PREFERRED EMBODIMENT

Reference numeral 1 refers to a so-called artificial kidney which contains blood liquid and which, by a diaphragm 2, is divided into two compartments. The right-hand compartment is connected to a pump P2 and is a portion of the so-called external circuit which is of no interest in the present context, whereas the left-hand compartment is in the patient circuit. The patient circuit also comprises a pump P1 and an air separator 3 as well as the necessary tube and hose connections. There is no need here to discuss the structural or operational features of those components because, on the one hand, they do not form any part of the present invention and, on the other, the corresponding know-how is elementary to manufacturers of the equipment here under discussion.

Numerals 4 and 5 refer to two cannule connected to a vein and to an artery, respectively, in the arm of the patient whereby a portion of his blood circulation system will form part of the circuit. Pump P1 which as shown on the drawing is connected between the artery cannula 5 and the artificial kidney 1 is in this embodiment driven by an electric motor M.

Air separator 3 is in the shape of a float chamber having a float 6. The density of the float is balanced so as to be just insignificantly less than and average value of the blood density. As has been mentioned above, the result thereof is that the float — which is suitably generally cylindrical and of considerable axial length — will have its major portion submerged in the blood liquid so that just a small portion projects above the liquid level. Blood entering the air separator 3 from tube 7 connected between the artificial kidney and the air separator 3 will drip down into the float chamber, air being separated in the process. The separated air collects in the top portion of the float chamber communicating with a contact manometer 8 the contact members of which are normally held separated, thus preventing current flow through the winding of a relay R, the energization circuit of which is fed by a power source 9.

The relay R controls two circuits also fed by source 9. The first circuit comprises an alarm device, here shown as an accoustic horn 12, and a relay make contact 10. In other words, in the normal state of the device the energization circuit of horn 12 is interrupted at contact 10. The second relay-controlled circuit, likewise connected to source 9, supplies current to motor M over relay break contact 11.

The operation of the device above described will now be described. Let it be assumed that in response to the presence of a large amount of air accumulated in the top portion of the float chamber, the level of the blood liquid therein is depressed to such an extent that the bottom of float 6 comes into contact with the bottom wall of the float chamber. As is realized, this causes a closing of the outlet tube 19 connecting the bottom portion of the float chamber with the vein cannula 4.

When, upon closing of the valve, the pump continues operating the result will be a pressure increase in the top portion of the float chamber. That pressure build-up is detected by manometer 8. At a predetermined pressure value an electrical circuit is closed through manometer 8 via current source 9 and the winding of relay R. The relay is consequently energized whereby contact 10 is closed and alarm device 12 activated. In this way the staff responsible for the operation of the machine is alerted about the fact that the blood circulation through the patient circuit of the apparatus has become discontinued. As is understood, the relay activation also opens contact 11 whereby motor M driving pump P1 is deenergized.

The float 6 can be looked upon as constituting a valve member and the inlet orifice of tube 19 can be considered to form a valve opening surrounded by a seat formed by the flat bottom of the float chamber. The two sealing surfaces should preferably be flat and relatively large. Practical tests have shown that such a design yields a most efficient sealing. On the other hand, it should be observed that a particular advantage of the invention is that the operation of the device remains completely satisfactory from a safety point of view also if, for some reason, the sealing would not be perfect. The reason for this is that even if a certain leakage past the valve seat occurs, the increase of the flow resistance still remains that great so the corresponding pressure increase is fully detectable by manometer 8 or, stated in other words, an alarm signal is always generated.

What is claimed is:

1. A dialysis apparatus, such as an artificial kidney, comprising:
    a circuit through which liquid blood is passed, said circuit including:
        a pump ($P_1$) coupled in said circuit for transporting blood through said circuit;
        a ventless float chamber (3) having an inlet at the upper portion thereof for receiving liquid blood and which is coupled in said circuit downstream of said pump, and a blood outlet in the bottom wall of said float chamber (3), said float chamber (3) always having a quantity of liquid blood therein; and
    means for coupling a portion of a patient's blood circulation system to said blood outlet of said float chamber (3) and to said pump ($P_1$) to close said circuit through which said blood is passed;
    a float (6) within said ventless float chamber (3), said float (6) having a density slightly less than the mean value of the density of the liquid blood in said float chamber (3) so that the major portion of said float (6) will normally remain submerged in the liquid blood within said float chamber (3), said float (6) having a lower surface which is arranged to at least substantially block said outlet of said float chamber to at least substantially interrupt the supply of blood from said outlet of said float chamber responsive to a lowering of said float in the blood in said float chamber caused by a predetermined increase of air pressure above the blood in said float chamber; and
    an alarm signal device comprising:
        detection means (8) coupled to said float chamber (3) for detecting a further predetermined increase in air pressure inside said float chamber (3) after a lowering of said float (6) which substantially blocks said blood outlet and which thereby substantially interrupts the blood supply to the patient's blood circulation system; and
        electrical means (R, 9, 12) coupled to said detection means (8) for generating an alarm signal in response to said detection of said further predetermined increase in air pressure in said float chamber (3).

2. A dialysis apparatus according to claim 1 wherein said electrical means further includes means coupled to said pump for turning off said pump in response to said detection of said further predetermined increase in air pressure in said float chamber.

3. A device as claimed in claim 1, in which the bottom of said float and a portion of the bottom wall of said float chamber surrounding said outlet connected to the patient's blood circulation system together form a valve normally held open but which is closed when the pressure of air inside said float chamber exceeds a predetermined value.

4. A device as claimed in claim 1, in which said detection means includes a manometer; and said electrical means comprises a set of contacts of said manometer which close when a predetermined air pressure is detected, a relay coupled to and being energized in response to closure of said contacts of said manometer, and accoustic signal means coupled to said relay and being operative in response to energization of said relay.

5. A device as claimed in claim 4, in which said relay further includes contact means coupled to said pump for turning said pump off when said relay is energized.

6. A device as claimed in claim 5, in which said contact means coupled to said pump is coupled to the power supply circuit for said pump for interrupting the power to said pump when said relay is energized.

7. A device as claimed in claim 5, in which said pump includes an electric motor and said contact means of said relay interrupts the power supply to said electric motor when said relay is energized.

* * * * *